United States Patent
Njemanze (12) 
(10) Patent No.: US 6,663,571 B1
(45) Date of Patent: Dec. 16, 2003

(54) TRANSCRANIAL DOPPLER ULTRASOUND DEVICE FOR ODOR EVALUATION

(76) Inventor: Philip Chidi Njemanze, No. 1 Uratta/MCC Road, P.O. Box 302, Owerri 1MO (NG)

(*) Notice: Subject to any disclaimer, the term of this patent is extended or adjusted under 35 U.S.C. 154(b) by 11 days.

(21) Appl. No.: 10/155,079

(22) Filed: May 28, 2002

(51) Int. Cl.[7] .............................. A61B 5/02; A61B 8/12
(52) U.S. Cl. ........................ 600/504; 600/454; 600/453
(58) Field of Search ................................ 600/504, 453, 600/454, 455, 456, 457

(56) References Cited

U.S. PATENT DOCUMENTS 6,258,032 B1 * 7/2001 Hammesfahr ............... 600/454
6,328,694 B1 * 12/2001 Michaeli ..................... 600/438

* cited by examiner

Primary Examiner—Max F. Hindenburg
Assistant Examiner—Navin Natnithithadha (57) ABSTRACT

The present invention is related to cerebral blood flow velocity monitoring method and system, specifically a transcranial Doppler device for odor matching and odor selection in canine and human subjects. The method and system is non-invasive with high temporal resolution, user-friendly and portable, including steps of obtaining a subject's baseline mean blood flow velocity in cerebral arteries using transcranial Doppler instrument with sample volume focused on cerebral vessels on both sides using two probes placed on the temples and calculating laterality index for both arteries. Simultaneously, testing the subject with odors while monitoring mean blood flow velocity during each odor in real-time. The acquired data is processed using an operatively attached microprocessor and using a cellular telephone to communicate the results to a computer workstation for further data analysis and storage.

20 Claims, 6 Drawing Sheets

TRANSCRANIAL DOPPLER ULTRASOUND DEVICE FOR ODOR EVALUATION

CROSS-REFERENCE TO RELATED APPLICATION

U.S. PATENT DOCUMENTS

U.S. Pat. No. 6,298,263) Oct. 10, 2001 Sedgwick et al. 600/544

OTHER PUBLICATIONS

Aaslid R. *Transcranial Doppler Sonography*. Wien: Springer-Verlag (1986).
Bloor B. M., et al. *Circulation*. 33/34 (supplementary II), 28–34, (1966).
Brisbin Jr I. L., & Austad S. N. *Animal Behavior*, 46, 191, (1993).
Brisbin Jr I. L., et al. *Science*, 290, 1093, (2000).
Carmichael S. T. et al., *Journal of Comparative Neurology*, 346, 403–434, (1994).
Dade L. A. et al. *Annals of the New York Academy of Sciences*, 855, 572–574 (1998).
Njemanze P. C. *Brain and Language*, 41, 367–380 (1991).
Njemanze P. C., et al., *Cortex*, 28, 69–75 (1992).
Oldfield R. C. *Neuropsychologia*, 9, 97–114, (1971).
Romanski L. M. et al. *Journal of Comparative Neurology*, 403, 141–157, (1999).
Roush W. *Science*, 279, 2042 (1998).
Royet J-P., et al. The *Journal of Neuroscience*, 20, 7752–7759, (2000).
Schoon G. A. A. *Applied Animal Behavioral Science*, 49, 257, (1996).
Schoon G. A. A., & deBruin J. C., *Forensic Science International*, 69, 111, (1994).
State v. Eugene Wiley, Case No. 8001659, 18th Judicial Circuit, Brevard County Fla. (1982).
State v. Kevin Roscoe, CR-127656, 11-20-90, Maricopa County, Arizona Superior Court, Judge Paulson.
Taslitz A. E., *Hastings Law Journal*, 42, 15, (1990).
Widder B. *Journal of Neurology, Neurosurgery and Psychiatry*, 52, 38–42, (1989).
Zald D. H., et al. *Journal of Neuropsychiatry*, 8, 249–261, (1996).
Zald D. H., & Pardc J. V. *Proceedings of the National Academy of Sciences of the United States of America*, 94, 4119–4124, (1977).
Zatorre R. J., et al. Nature, 360, 339–340, (1992).

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

The present invention is related to cerebral blood flow velocity monitoring method and system, specifically a transcranial Doppler (TCD) device for odor matching and odor selection.

In the field of forensics, odor evaluation can make important contributions in both prosecution and defense of criminal cases. The use of blood hounds and other scent following dogs to identify individual people or their scent trails in the environment on the basis of a previous offered reference scent article such as handkerchief, hat, and other items of clothing has been described by A. E. Taslitz, in an article published in *Hastings Law Journal*, volume 42, page 15. (1990). Canine scent identification evidence is usually presented in court to suggest the unique identification of an accused individual in the same way that finger prints are used as discussed in an article by I. L. Brisbin Jr et al., published in *Science*, volume 290, page 1093, (2000). Canine scent identification evidence is premised on the alleged factuality of the "individual odor theory," which hold that each person has a unique scent that can be identified by the dog and related back to a specific individual. Courts have accepted the performance of canine scent identification, even when it is claimed that they are detecting the scent of a specific individual at the scene of a crime nearly 2 years after the crime was committed as discussed in the case State v. Eugene Wiley Case No. 8001659, 18th Judicial Circuit, Brevard County Fla. (1982). However, juries have found individuals guilty almost solely on the basis of dog evidence subsequently shown to be unreliable, if not fraudulent as in the case State v. Kevin Roscoe, CR-127656, 11-20-90, Maricopa County, Arizona Superior Court, Judge Paulson. It is therefore imperative that further research studies of the abilities of such scenting dogs be undertaken. Especially, the ability to scent match odors from individuals to handled objects, under controlled laboratory conditions as described in articles by G. A. A. Schoon, J. C. deBruin published in *Forensic Science International*, volume 69, page 111, (1994); and G. A. A. Schoon, *Applied Animal Behavioral Science*, volume 49, page 257, (1996).

However, in some studies dogs have proven capable of performing such scent matching tasks at levels greater than chance, their error rates are seldom more than 10 to 20% as discussed in an article by I. L. Brisbin Jr. and S. N. Austad, *Animal Behavior* volume 46, page 191, (1993). Errors may also be introduced by the interpretation of the behavioral response of the dog. What is probably lacking is an objective physiologic correlate of scent matching odors in canine detectives. The latter is the subject matter of the present invention.

There is thus ample evidence that in primates olfactory memory has several unique characteristics, the most striking being its resistance to decay over long intervals, suggesting a specialized memory system. However, investigations into the neural substrates of human olfactory memory have been limited. Previous positron emission tomography (PET) studies have shown significant regional cerebral blood flow (rCBF) increases during olfactory stimulation: unilateral in the right orbitofrontal cortex (OFC), and bilaterally in the inferior frontal and temporal lobes (piriform cortex) as described in an article by L. A. Dade, et al. entitled "Human brain function during odor encoding and recognition: a PET study," published in *Annals of the New York Academy of Sciences*, volume 855, pages 572–574, (1998).

U.S. Pat. No. 6,298,263 describes an apparatus and method for odor selection to match a visual and auditory stimulus while monitoring electrical brain activity preferably event related potentials (ERPs) using electroencephalography (EEG). In accordance with '263 patent, spontaneous EEG has been used to show correlation between psychometric properties of odor and spontaneous brain activity in real time following olfactory events. Furthermore, rCBF changes associated with olfactory sensing has been described in an article by L. A. Dade, et al. entitled "Human brain function during odor encoding and recognition: a PET study," published in *Annals of the New York Academy of Sciences*, volume 855, pages 572–574 (1998). rCBI has been shown to correlate with cerebral blood flow velocity measurements monitored using transcranial Doppler ultrasound (TCD) as described in a book by R. Aaslid, entitled "Transcranial Doppler Sonography," published in Wien, by Springer-Verlag (1986).

One object of the present invention is to perform odor matching tasks in primates. The use of blood hounds and other scent following dogs to identify individual people or their scent trails in the environment on the basis of a previously offered reference scent article such as handkerchief hat, and other items of clothing as described by A. E. Taslitz in an article published in *Hastings Law Journal*, volume 42, page 15, (1990). The cerebral arteries in dogs could be evaluated using TFCD in much the same manner as in humans as described in a book by R. Aaslid, entitled "Transcranial Doppler Sonography" published in Wien, by Springer-Verlag (1986). Odor matching tasks in canines could be used in forensic analysis of crime scenes as described by A. E. Taslitz. in an article published in *Hastings Law Journal*, volume 42, page 15, (1990).

A further object of the present invention is its use in the design of fragrance. It is increasingly important that fragrances be designed to evoke a specific "emotional content." The desired emotional content is a product of brain physiologic response more specifically induced lateralization of rCBF. In other words, the anatomy and behavioral features of olfactory (smell) processing suggest that hedonically (pleasantness-unpleasantness) valenced olfactory stimuli may be tested. In an example described in an article by D. H. Zald and J. V. Pardc entitled "Emotional olfaction, and the human amygadala: Amygdala activation during aversive olfactory stimulation," published in *Proceedings of the National Academy of Sciences of the United States of America*, volume 94, No. 8, pages 4119–4124 (1977), exposure to highly aversive (punishing) odorant produced strong rCBF increases in both amygadala and in the left OFC. Exposure to less aversive odorants produced rCBF increases in the OFC but not in the amygdala. Furthermore, the activity within the left amygdala was associated significantly with subjective ratios of perceived aversiveness. The comparison of fragrances involves the use of working memory for odors, and could thus be said that the present invention measures at least in part the working memory for odors.

A further object of the present invention is its use in the design of products that include multiple modality sensing. Transcranial Doppler ultrasonography, a main component of the present invention has been used for the assessment of auditory stimuli such as music as described in an article by P. C. Njemanze entitled "Cerebral lateralization in linguistic and nonlinguistic Perception: Analysis of cognitive styles in the auditory modality" published in *Brain and Language*, volume 41, pages 367–380, (1991), as well as in the visual modality as described in an article by P. C. Njemanze et at., entitled "Cerebral lateralization and color perception: a transcranial Doppler study," published in *Cortex*, volume 28, pages 69–75, (1992). The application of the present invention in the advertisement industry could be further illustrated. Car designers may sometimes require to use all sensory modalities to uplift the esthetic value of their products. For example, it may be desirable that the visual outlook of the car, the smell within they car and the audio output of the sound system all have a combined positive cumulative effect on the buyer in the auto showroom, in other words, to improve the hedonic (pleasantness) rating. Since the evoked response of rCBF by emotionally valenced olfactory, visual and auditory stimuli all converge at the OFC, temporal pole and the superior frontal gyrus as described by J-P. Royet, et al. in an article entitled "Emotional responses to pleasant and unpleasant olfactory, visual, and auditory stimuli: a positron emission tomography study," published in *The Journal of Neuroscience*, volume 20, pages 7752–7759, (2000), it is plausible to measure rCBF in the anterior cerebral artery vascular territory that supplies the OFC and other areas of the olfactory cortex. Determination of the hedonic rating of these elements combined is the subject matter of the present invention. Similarly, home designers could improve home decorations by combining the effects of visual, auditory and olfactory modalities, which could be assessed by the present invention.

A further use of the present invention is to assess a cumulative response to visual, auditory and olfactory sensing in film production. Although films are usually produced to evoke auditory and visual effects, most of the olfactory sensing is imaginary and does not add to the overall effects of the film. The present invention makes it possible to assess what brain physiologic effect may be added if short bursts of odors are introduced through the cinema ventilation system and expressly vacuumed out at the appropriate audiovisual scenes of the film within a specialized film theater. It may be desirable to increase the level of aversiveness (unpleasantness) of the odor that accompanies some audiovisual scenes in a horror movie, while love stories may require pleasant odors to get the story across. The introduction of this approach in the film industry and the possibility of measuring brain physiologic responses to them will have a notable effect in the advertisement of products on specialized cinema screens. It could be possible to introduce bursts of the scent of an advertised soap or fragrance via the cinema ventilation system and quickly removing it using the vacuum system. This introduces a real world experience especially with 3D images and high definition TV movies.

Another use of the device could be illustrated by product presentations at exhibition shows. A model presenting a new product may have the makeup that will synergistically augment visual and olfactory sensing effects along with specially selected audio effects at an exhibition center by way of example.

Another use of the present invention may be in the food industry for packaging of canned foods and drinks. The aroma of the foods and drinks (such as coffee, tea, alcohol beverages, soft drinks etc.) may have a decisive influence on the consumer. Aroma of foods stimulates appetite. It is therefore desirable to enhance the smell of foods to stimulate appetite and condition a general feeling of pleasantness. The present invention permits the evaluation of the hedonic ratings of different aromas of foods and drinks.

SUMMARY OF THE INVENTION

The present invention provides a method and system for odor matching and odor selection comprising testing a subject (human or canine) by presenting the subject with one or more odors under different conditions, while monitoring cerebral blood flow velocity of the subject during odor tasks.

The special embodiment of this invention is illustrated in the specification, it includes block and schematic diagrams for the format of the instrumentation, and how the system functions is shown by way of example. The subject refers to a human or canine under testing by way of example. The system comprises an odor administration container, transcranial Doppler ultrasound device operatively connected to a microcomputer and cellular telephone and a main frame data analysis computer. The present invention uses a conventional transcranial Doppler instrument with pulsed wave 2 MHz ultrasound transducer or probe. The transcranial Doppler ultrasound probes are placed on the acoustic window of the temporal bone above the zygomatic arc on both sides of the head and focused on major cerebral vessels such as both anterior cerebral arteries (ACAs) by way of example. The transcranial Doppler device is modified to allow canine and human subjects to move freely following an odor trail at a crime scene by means of integrating a microcomputer and a cellular phone circuitry to the conventional circuitry of the transcranial Doppler instrument creating a system and method of transcranial Doppler device with wireless communication to the main frame computer either directly or via the internet in real time.

These and other objects of the invention may become apparent to those skilled in the art upon reviewing the description of the invention as set forth hereinafter, in view of its drawing.

DETAILED DESCRIPTION OF THE INVENTION

Figure 1A:
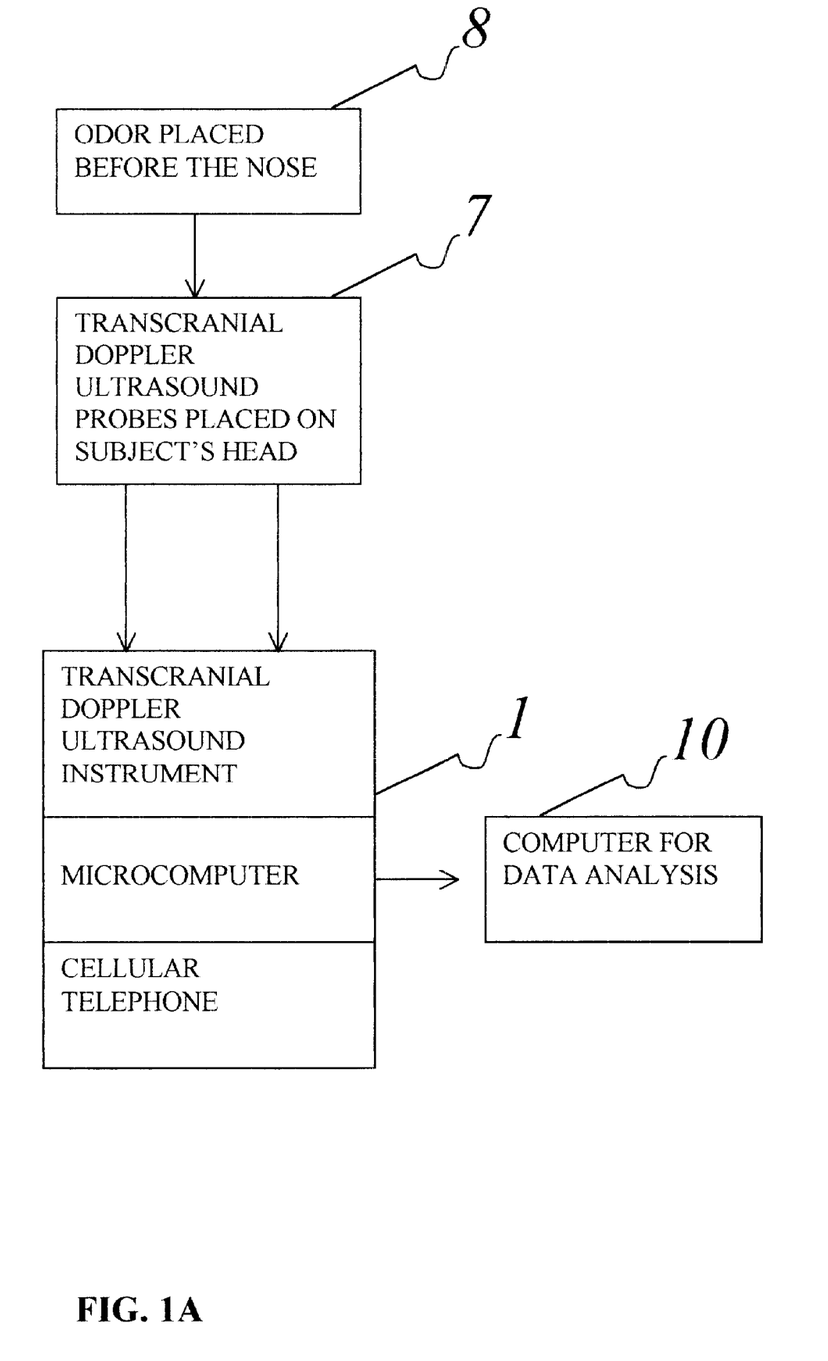
FIG. 1A shows the schematic diagram of the present invention.

The block diagram of the present invention is illustrated in FIG. 1. As shown therein, a transcranial Doppler device with microcomputer and cellular telephone circuitry integrated within 1, has attached transcranial Doppler ultrasound probes 7 suspended on a head set placed on the head of a subject, on the temporal bones above the zygomatic arc. The integrated device 1 is telemetrically connected to a computer 10 for real-time data transfer, analysis and storage. The ultrasound sample volume for isonation is placed in the main stem of the ACAs from both sides at a depth range varying from 65–70 mm by way of example. The probes are covered with ultrasonic gel pads to enhance tissue coupling. The headset may be equipped to steer the probe manually or automatically by a microcomputer operatively connected to the transcranial Doppler instrument. A miniaturized transcranial Doppler instrument with bilateral ultrasound probes operatively controlled by a microcomputer could be obtained from a company called DWL (Sipplingen, Germany) by way of example. The microcomputer and cellular phone circuitry communicates the measured cerebral blood flow velocities to a personal computer 10 or a main frame computer workstation for example the Federal Bureau of Investigation (FBI) crime database, which could integrate the online data to established profiles for reference odors. The online odors are administered from a container placed close to the nostrils.

Figure 1B:
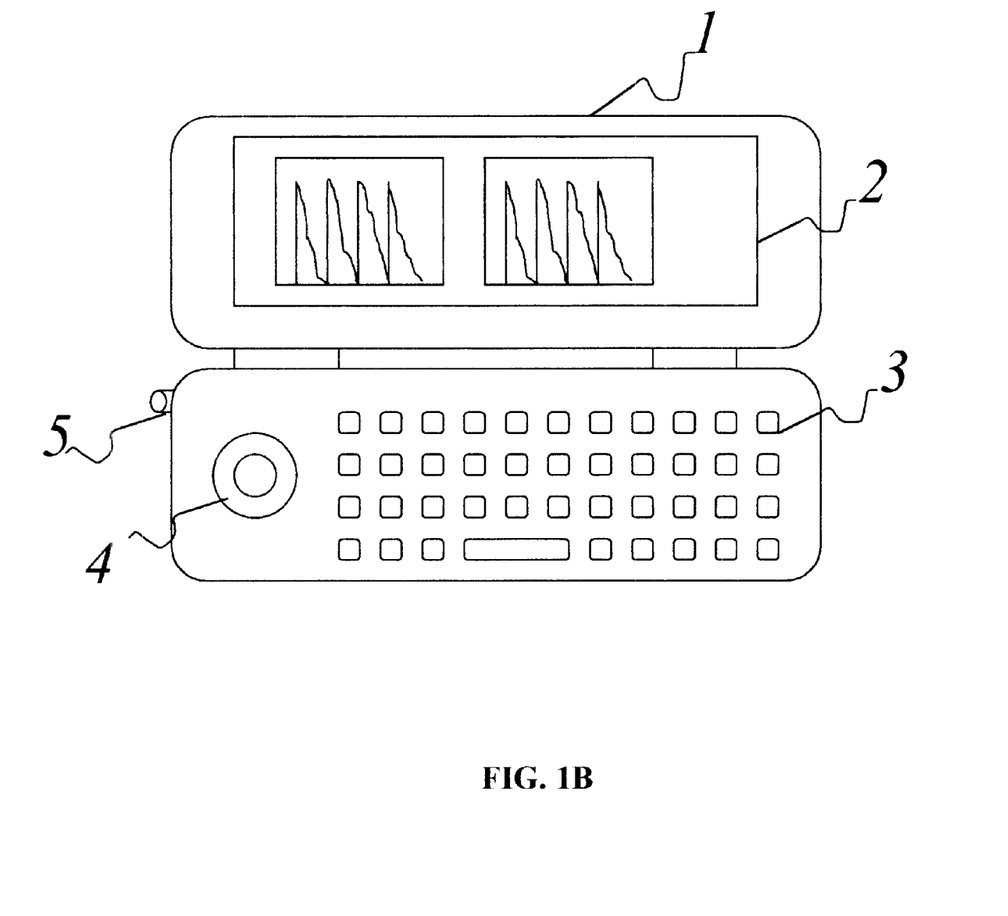
FIG. 1B shows the front inner view of the present invention.
Figure 2:
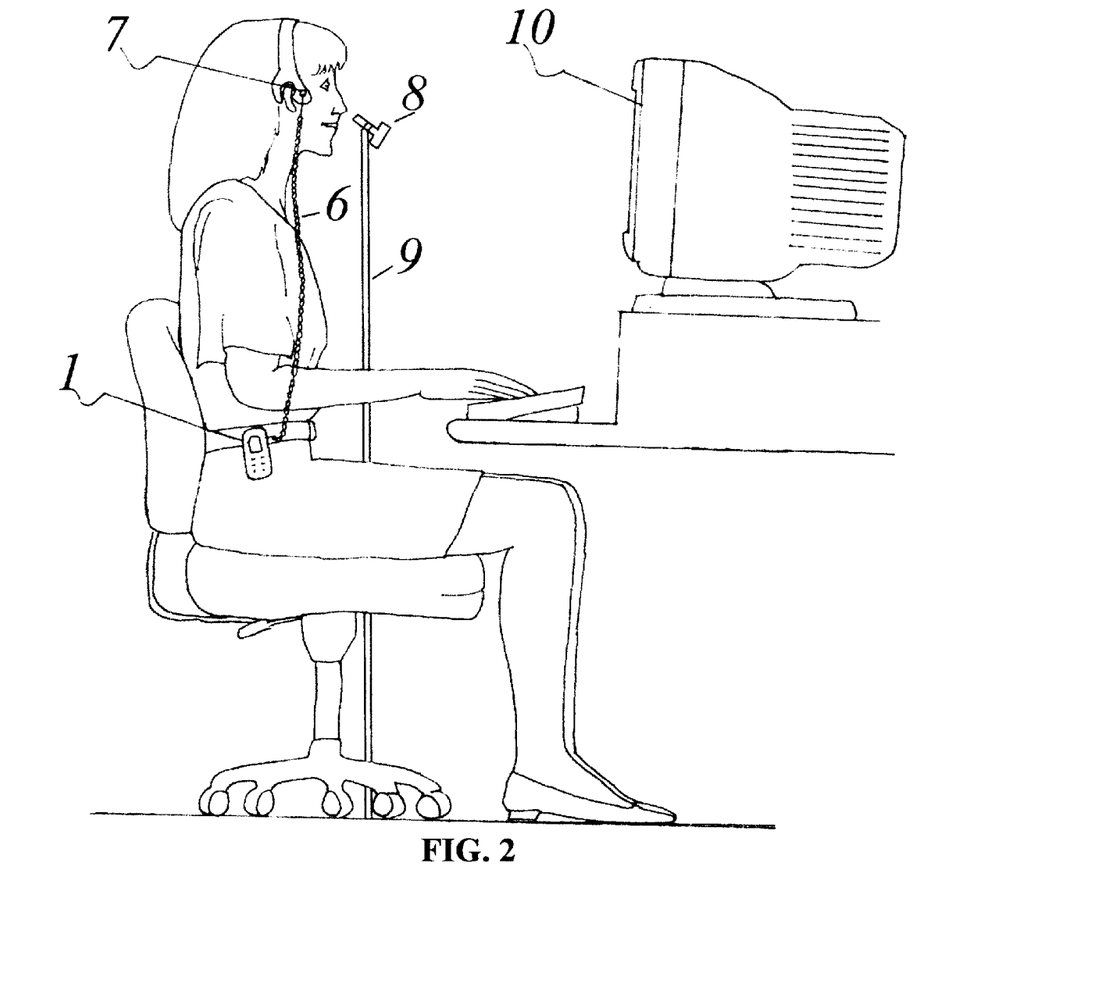
FIG. 2 shows a subject setup with the present invention.

As shown in FIG. 1B, the transcranial Doppler device 1 has the normal features of a computer with monitor display 2 showing Doppler velocity profiles, a keyboard 3 and a loudspeaker 4 to produce audible Doppler signals. The communication to the computer workstation is facilitated via an integrated cellular phone with an antenna 5. FIG. 2 shows the interface of the present invention with a subject. The headset is placed on the head with ultrasound probes 7 held in place in the left and right arms of the headset and placed on the temporal bones on both sides of the head. The transducer cable 6 is attached to the transcranial Doppler device. The subject is presented with the odor 8 under investigation and in some cases simultaneously with auditory and visual stimuli presented on a computer monitor 10.

Figure 3:
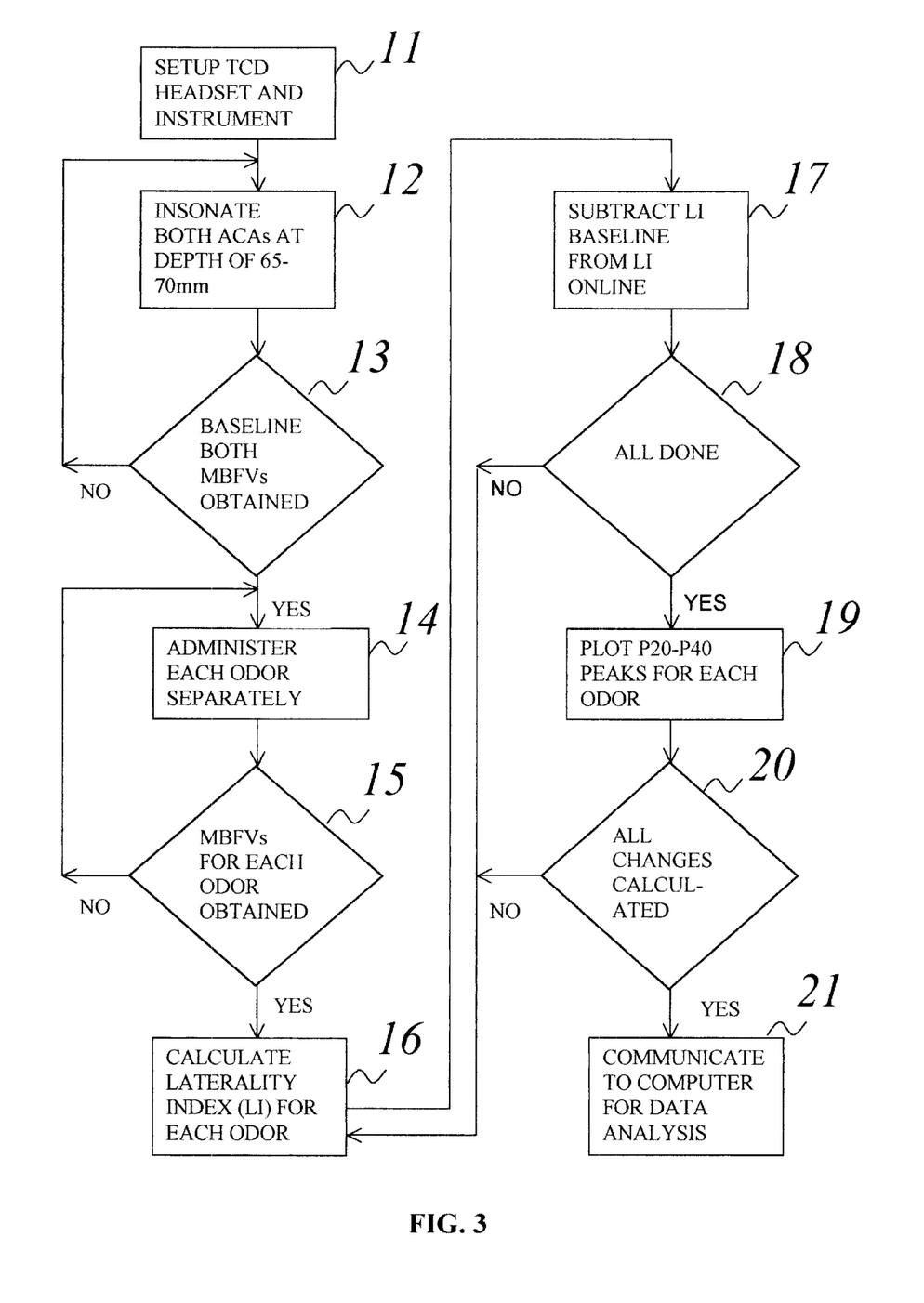
FIG. 3 shows the program flow chart of the invention.

FIG. 3 shows the functional flow chart of the present invention by way of example. The subject is setup with the headset and transcranial Doppler (TCD) instrument 11, with the probes isonating both ACAs at a depth of 65–70 mm in most subjects. The baseline of both mean blood flow velocities (MBFVs) are obtained 13, if not all are obtained the system repeats the isonation of step 12. Thereafter the separate odors are administered to the subject 14 and MBFVs obtained for each odor 15, if not all are obtained 15 the previous step 14 is repeated. Thereafter the laterality index (LI) at different stimulus duration for each odor is calculated 16 for both baseline and experimental conditions and the difference calculated between baseline and online values 17. If not all are calculated 18, the systems repeats the preceding steps 16–17. Thereafter the system plots the peak changes in LI at the time interval 20–40 seconds following stimulus administration referred to here as P20–P40 peaks for each odor 19. If not all are calculated 20, the system repeats the preceding steps 16–19. Thereafter the results of the P20–P40 peaks are communicated to the computer workstation 21 for odor selection by hedonic rating or odor matching of LI peaks for a specific odor relative to a target odor.

Materials and Methods

Simultaneous bilateral TCD ultrasound was used to measure mean blood flow velocities (MBFV) in the right and left anterior cerebral arteries (ACA) in right-handed normal subjects. The preferred hand was determined using the Edinburgh handedness inventory as described by R. C. Oldfield, in an article entitled "The assessment and analysis of handedness: The Edinburgh Inventory." published in *Netropsychologia*, volume 9, pages 97–114, (1971). The population consisted of 20 subjects (mean±SD age= 24.3±2.72 years) of which 10 were females (mean±SD age=25.52±2.97 years) and 10 were males (mean±SD age= 23±1.83 years). There was no history of neurologic or cardiovascular or respiratory diseases in the study cohort. No subject had any history of lone use of any medication. None ingested caffeine at least 24 hrs prior to the study. All were non-smokers and had no history of alcohol abuse. All have had 12 to 18 years of schooling. Informed consent was provided to all subjects according to the Declaration of Helsinki, and the Institutional Ethical Committee guidelines.

Scanning Procedure

All TCD procedures were performed using examination techniques described for cognitive studies (Njeemanze, 1991). The transcranial Doppler scanning was performed using a bilateral simultaneous TCD instrument (Multi-Dop T, DWL, Sipplingen. Germany). All subjects were briefed on the protocol for the entire experiment and all questions and practice sessions on what was required for the odor paradigm were explained prior to start of the experimental data acquisition. All TCD studies were performed as follows: first, the subject was placed in supine posture with head up at 30 degrees. The probe holder headgear—ILAM-Rack was used with base support on two earplugs and on the nasal ridge. Two 2 MHz probes were affixed in the probe holder and isonation performed to determine the optimal position for continuous isonation of both ACA main stems at 65 mm depth from the surface of the probe. Flow direction was confirmed as away from the probe and using for orientation the flow in the internal carotid artery (ICA) seen as towards the probe at the bifurcation. All gain and power settings were kept constant for both ACAs in all subjects. The probes were placed firmly on the subject's head and were locked in position after adjusting the lever and tightening the knurled screw from both sides. Comfort of the subject within the headgear was assured prior to start of recording. Subjects were blindfolded and instructed to remain mute and not to move throughout the data acquisition time duration. All environmental noise including sound from the TCD instrument was excluded with additional ear plugs, and environmental luminance was kept constant for all participants. Electrocardiographic monitoring of pulse and respiratory rate along with self-perceived anxiety levels were recorded during the study to control for effects on results.

Baseline Study

The baseline condition was dark as subject remained blindfolded and was instructed to smell without any odor being presented. The subject was aware that the initial recording was resting baseline and did not expect any odor. A continuous train of velocity waveform envelopes was recorded at resting baseline with the subject mute, still and blindfolded with a smell task with no odor presented. These baseline recordings were obtained prior to stimuli administration. TCD baseline measurements were made for 60 seconds.

Odor Paradigm

Tile odor paradigms comprised a test battery comprising five female fragrances (Sunflower from Elizabeth Arden Co, Dist. New York, N.Y. 10105; Poison eau de cologne from Christian Dior, 75008 Paris; Elizabeth Arden Splendor eau de perfum from Elizabeth Arden Co, Dist. New York, N.Y. 10105; COCO eau de toilette from Chanel, Paris; and Wings from extraordinary eau de toilette from Giorgio Beverly Hills Dist. Beverly Hills, Calif. 90210); five male fragrances (English leather cologne from MEM Company, Inc. Northvale, N.J. 07647; Fahrenheit after-shave lotion from Christian Dior 75008 Paris; Stetson sierra for men cologne from Cor US Inc. New York, N.Y.; Guess men after shave from Revlon New York; and Clinique perfume from Clinique Labs Dist. New York, N.Y.), five food spices (thyme, curry, ginger, nutmeg, and onions) and five common household chemicals (vinegar, spirit, dettol, bleach and formalin). The odors were administered birhinally (on both nostrils) for a duration of one second at each nostril, starting at the beginning of recording. Odors were administered from a container placed at 1.5 cm from the nostrils. After administration of each odor it was quickly removed from the room to prevent long time decay effects. A continuous train of velocity waveform envelopes was recorded with the subject mute, still and attention focused on perceiving the odor and rating the odor on a subjective hedonic (pleasantness) rating scale of 1–5 (1-very unpleasant, 2-unpleasant, 3-fair, 4-pleasant and 5-very pleasant). The subject indicated the choice by slightly raising one of the corresponding fingers 1–5 on one hand. An observer recorded the finger corresponding to the rating. The hand where the fingers were raised was pseudo-randomized such that there were equal subjects raising the right and left hand for the same number of odor sets. TCD stimuli measurements were made for 60 seconds.

Breathholding Task

The carbon dioxide tension in the blood alters cerebral blood flow significantly as described in an article by Bloor et al. entitled "Relationship of cerebrovascular reactivity to degree of extracranial vascular occlusion", published in *Circulation*, volume 33/34 (supplementary II), pages 28–34, (1966). Hypercapnia was induced by asking the subjects to hold their breath and close their nostrils with both index fingers and to discontinue voluntarily. The use of both index fingers eliminated possible motor activity induced asymmetry. The percentage change of MBFV relative to resting baseline values was calculated as:

%dMBFV=((MBFV hypoventilation−MBFV baseline)/MFBV baseline)*100.

The percentage of dMBFV was calculated for left (L) and right (R) MCA. Depending on the side with the greater percentage change, the set was noted as either L>R and R>L or L=R. It has been suggested that neocortical vascularization which develops in conjunction with the nervous system and phylogenetic trends may share similar dominance characteristics as discussed by P. C. Njemanize, in an article entitled "Cerebral lateralization in linguistic and Nonlinguistic perception: analysis of cognitive styles in the auditory modality," published in *Brain and Language*, volume 41, pages 367–380, (1991). Recent evidence might indicate an unexpected level of coordination between the developing nervous and circulatory systems as discussed by W. Roush in an article entitled "Receptor link blood vessels, Axons," published in *Science*, volume 279, pages 2042, (1998).

Probably, the physiologically dominant hemisphere will have a greater neocortical vascularization, this means greater resistance arterioles and therefore a lesser capacity to increase blood flow velocity in response to $CO_2$ tension, which is known to rive a measure of the capacity of the intracerebral arterioles to dilate as described in studies by B. Widder in an article entitled "The Doppler $CO_2$ test to exclude patients not in need of extracranial/intracranial bypass surgery," published in *Journal of Neurology, Neurosurgery and Psychiatry*, volume 52, pages 38–42, (1989). Thus subjects with L>R were said to have physiologic right-hemisphere dominance. Conversely, subjects with R>L were said to have physiologic left-hemisphere dominance. The subjects with L=R were considered void of vascular hemisphere dominance. The importance of physiologic hemisphere dominance and linguistic processing has been discussed by P. C. Njemanze, in an article entitled "Cerebral lateralization in linguistic and Nonlinguilstic perception: analysis of cognitive styles in the auditory modality." published in *Brain and Language*, volume 41, pages 367–380. (1991).

Calculations

Cerebral lateralization was assessed by side-to-side differences in mean flow velocity given as laterality index (LI') by way of example and expressed as:

LI'=(Left $MBFV_{10sec}$−Right $MBFV_{10sec}$/(Left $MBFV_{10sec}$+Right $MBFV_{10sec}$))*100.

The actual magnitude of lateralization (LI) for each 10 seconds segment for each task was calculated as the difference between LI' values measured during the 10 seconds segment of the task and the corresponding 10 seconds segment of rest (onset of resting baseline corresponds with onset of task within the 60 seconds):

LI=LI'task$_{10sec}$–LI'baseline$_{10sec}$.

In general, positive LI values suggests a left lateralization, while negative LI values suggests a right lateralization. Zero LI values showed no lateralization from the resting condition or possible bilateral response. The calculated LI were designated as LI$_{0-10sec}$, LI$_{11-20sec}$, LI$_{21-30sec}$, LI$_{31-40sec}$, LI$_{41-50sec}$, LI$_{51-60sec}$, for values measured for time segment 0–10 seconds, 11–20 seconds, 21–30 seconds, 31–40 seconds, 41–50 seconds, 51–60 seconds respectively. The corresponding peaks were designated as P10, P20, P30, P40, P50 and P60 respectively.

Statistics

Results were given as mean±SD where applicable. To examine the effect of Gender, Breathholding and Time variables, the LI scores were analyzed by a 2-way analysis of variance (ANOVA) for repeated measures. The resulting design was a 2 (Gender: Female, Male) by 3 (Breathholding: R>L, L>R and R=L), by 6 (Time periods of 10 seconds each: 0–10s, 1–20s, 21–30s, 31–40s, 41–50s, the latter factor was a within-subject or repeated measures factor because it represents repeated measures at different time intervals in the same subject.

To examine the effect of Hedonic ratings at the different Time peaks, the LI values were further analyzed in a separate 2-way ANOVA for repeated measures. The resulting ANOVA design was a 5 (Hedonic ratings: 1-very unpleasant. 2-unpleasant, 3-fair, 4-pleasant and 5-very pleasant) by 6 (Time periods of 10 seconds each: 0–10s, 11–20s, 21–30s, 31–40s, 41–50s, 51–60s intervals). The last factor was a within-subject or repeated measures factors because they represent repeated measurements of the effects of ratings at different time intervals in the same subject. The first factor is a between-group factor. In a separate comparison the difference in subjective Hedonic ratings for the different sets of odors were analyzed using ANOVA with one grouping variable odors comprising they twenty odors used (five female fragrances, five male fragrances five food spices, and five common household chemicals). Where applicable planned contrasts were performed between selected variables. All statistical calculations were performed using a statistical software package (Statistica, StatSoft, Oklahoma, USA).

RESULTS

Figure 4:
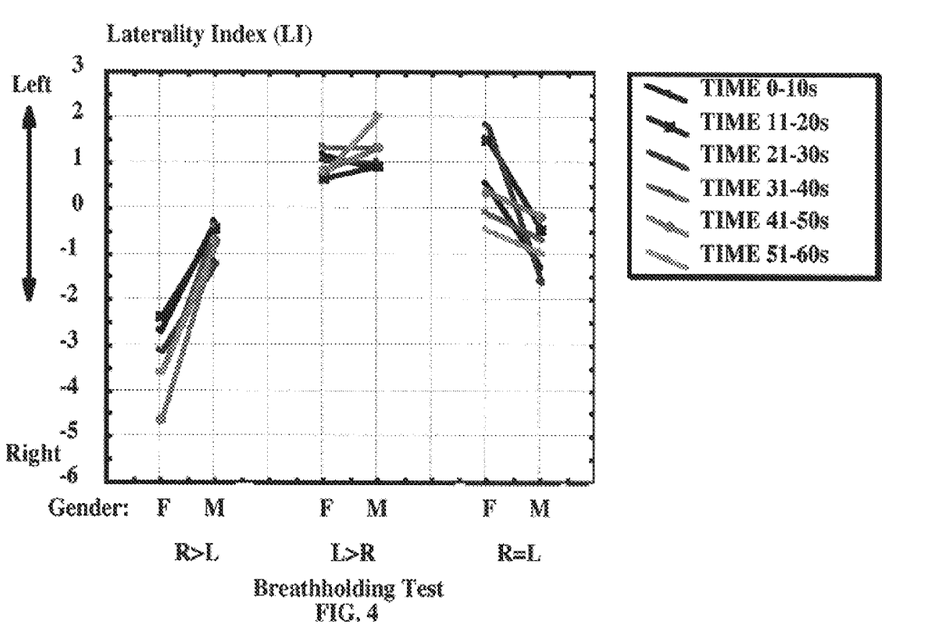
FIG. 4 shows the mean laterality index (LI) of the different time intervals for all odors for different stimulus duration in males and female subjects classified according to breathholding test.

FIG. 4 showns the mean LI of the six identified groups of subjects based on breathholding test: female of R>L (N=2), females of L>R (N=7), females L=R (N=1); Immales of R>L (=3), males of L>R (N=5), males of L=R (N=2). In other words subjects with physiologic left-hemisphere dominance were 5/20 or 25%; subjects with physiologic right-hemisphere dominance were 12/20 or 60%; and subjects with no physiologic dominance characteristics were 3/20 or 15%. The obtained ratios of physiologic hemisphere dominance seen in the ACA territory is the reverse of that seen in the middle cerebral artery territory obtained in separate cohort in an earlier study of language processing as discussed by P. C. Njemanze, in an article entitled "Cerebral lateralization in linguistic and nonlinguistic perception: analysis of cognitive styles in the auditory modality." published in *Brain and Language*, volume 41, pages 367–380, (1991). The striking reverse trend in dominance characteristics in specific vascular beds may well be because of the localization of language in the physiologic dominant left-hemisphere (61.5%) in the MCA territory in right handers. It may therefore be noted that while subjects may well be right physiologic dominant in the ACA territory, they may be left physiologic dominant in the MCA territory. A process that reflects the phylogenetic trends of development of the cerebral hemispheres and acquisition of functional asymmetry. However, the term hemisphere dominance may be in appropriate since it is in not universal for all vascular territories but rather limited to a vascular territory. A more preferred term is 'physiologic vascular dominance'.

The initial two-way ANOVA with repeated measures with design of 2 (Gender) by 3 (Breathholding), by 6 (Time periods of 10 seconds each) revealed a significant main effect of Gender $F(1,394)=6.1$, $p<0.013$, MSe=103.5. There was a significant main effect of Breathholding $F(2,394)=119.3$, $p<0.00000001$, MSe=2016.2. There was a significant main effect of Time $F(5,1970)=3.3$, $p<0.006$, MSe=7.97. There was a Gender×Breathholding interaction $F(2,394)=31.9$, $p<0.00000001$, MSe=538.8. There was a Gender×Time interaction $F(5,1970)=13.7$, $p<0.00000001$, MSe=33.3. There was a Breathholding×Time interaction $F(10,1970)=8.2$, $p<0.00000001$, MSe=19.9. There was a three way interaction of Gender×Breathholding×Time $F(10,1970)=3.9$, $p<0.00003$, MSe=9.4.

FIG. 4 revealed that in relation to odors subjects of set R>L with phlysiologic left-hemisphere dominance lateralized to the non-dominant right hemisphere with females showing a greater right hemisphere advantage than males. Conversely, subjects of set L>R with physiologic right-hemisphere dominance were lateralized to the non-dominant left hemisphere. Subjects of set L=R with no clear dominance characteristics showed only a tendency for left hemisphere advantage in females and right hemisphere advantage in males. In other words, the lateralization for odors was to the physiologic non-dominant hemisphere.

Figure 5:
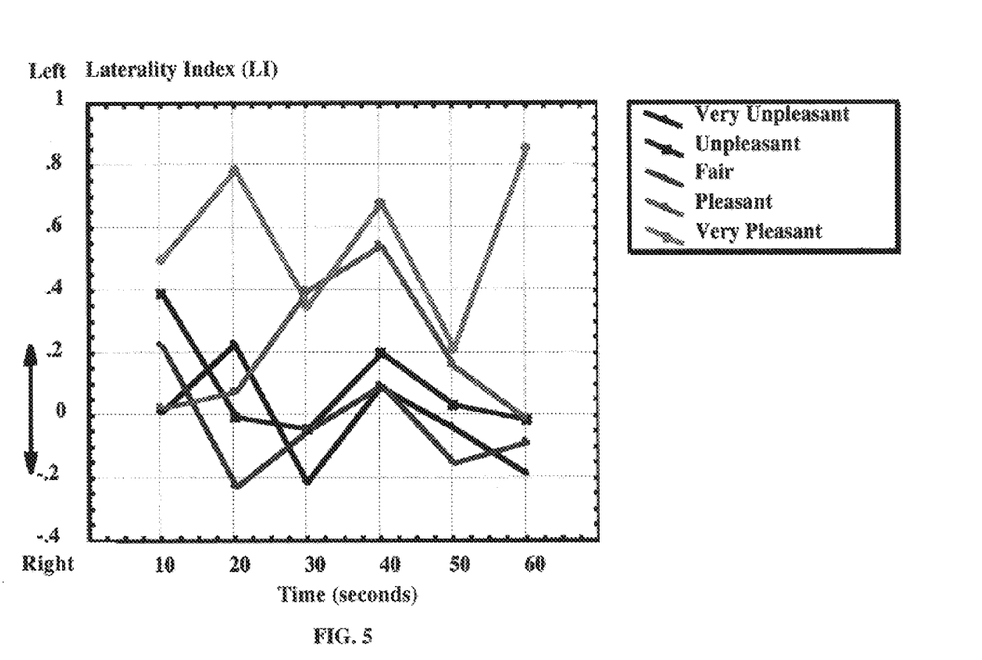
FIG. 5 shows the plot of mean laterality index (LI) of the different odors according to hedonic rating (pleasantness-unpleasantness) for the stimulus duration time.

The Hedonic ratings were compared for all the odors used in a separate ANOVA test. This revealed a major difference in the ratings for the odors $F(19,380)=10.98$, $p<0.00000001$, MSe=13.4. A second 2-way ANOVA test using LI values with a repeated measures design of 5 (Hedonic ratings) by 6 (Time periods of 10 seconds each) revealed no significant main effects of the Hedonic ratings ($p>0.05$) and Time ($p>0.05$). FIG. 5 shows a plot of the Hedonic ratings variation with Time. This plot revealed a clear separation of the Pleasant and Very Pleasant ratings at peaks of P20, P30 and P40 from the Fair, Unpleasant and Very Unpleasant categories. The P20–P40 peaks represents the time interval of maximal effect of the odor stimuli. Further planned contrasts using P20–P40 peaks confirmed a statistically significant difference between the Hedonic ratings $F(1,56)=5$, $p<0.029$, MSe=49.8. Furthermore, as shown in FIG. 5, odors with higher hedonic ratings varied by the degree of left hemispheric lateralization. Comparison of the present findings with previous PET tomography studies is reasonable, given the relationship of rCBF to mean cerebral blood flow velocity; however, some methodological and anatomic differences remain. While TCD blood flow velocity measurements is related to rCtBF the flow velocity integral measured in the main stem of the ACA generalizes changes in a hemispheric region, rather than specific structures. Conversely, the PET technique measures changes at specific anatomic substrates, which may individually show sometimes opposite trends in changes in blood flow. However, overall the changes should reflect the general trend. Both methods show that odors evoke detectable rCBF asymmetric responses. The TCD further clarifies that this could be to the right or left hemisphere provided it is the physiologic non-dominant hemisphere. This may help resolve the sometimes seemly contradictory findings on PET studies as described by J-P. Royet, et al. in an article entitled "Emotional responses to pleasant and unpleasant olfactory, visual, and auditory stimuli: a positron emission tomography study," published in *The Journal of Neuroscience*, volume 20, pages 7752–7759, (2000); and an article by L. A. Dade et al., entitled "Human brain function during odor encoding and recognition: a PET activation study," published in *Annals of the New York Academy of Sciences*, volume 855, pages 572–574. (1998). It however, appears from the results that while the right hemisphere is implicated in the basic processing of olfactory stimuli in 25% of subjects, the left hemisphere predominates in up to 60% of subjects. Furthermore, the left hemisphere appears to differentiate the hedonic ratings of odors. Both of these conclusions are consistent with previous PET findings by R. J. Zatorre. et al., entitled "Functional localization and lateralization of human olfactory cortex," published in *Nature*, volume 360, pages 339–340, (1992); and by D. H. Zald and J. V. Pardc, in an article entitled "Emotion, olfaction, and the human amygdala: amygdala activation during aversive olfactory stimulation," published in *Proceedings of the National Academy of Sciences USA*, volume 94, pages 4119–4119, (1997).

While a preferred embodiment of the present invention is described above, it is contemplated that numerous modifications may be made thereto for particular applications without departing from the spirit and scope of the present invention. Accordingly, it is intended that the embodiment described be considered only as illustrative of the present invention and that the scope thereof should not be limited thereto but be determined by reference to the claims hereinafter provided.

I claim:

1. A noninvasive method to determine the cerebral blood flow velocity response to odors by a human subject, including, steps of:
   (a) obtaining a subject's baseline cerebral blood flow velocity in cerebral arteries on both sides of the brain using a transcranial Doppler ultrasound instrument with two probes placed on the temples and sample volumes focused on cerebral vessels on both sides;
   (b) simultaneously with (a) obtaining the mean blood flow velocity in both pairs of cerebral arteries at baseline;
   (c) testing the subject with odor tasks while simultaneously monitoring the mean blood flow velocity during each task in real-time;
   (d) determining the response of the brain using mean cerebral blood flow velocity to a target odor:
   (e) determining the response of the brain using side-to-side differences in mean cerebral blood flow velocity to a target odor;
   (f) determining the response of the brain using side-to-side differences in mean cerebral blood flow velocity to a given odor;
   (g) simultaneously with (f) determining if there is a match of the response of the brain using side-to-side differences in mean cerbral blood flow velocity to a given odor compared to the response evoked by target odor; and
   (h) simultaneously with (g) assessing if by varying the intensity of the given odor the match in response to target odor could be enhanced.

2. The invention of claim 1 wherein the said device comprise a transcranial Doppler instrument means to acquire Doppler flow velocity waveforms used to calculate mean cerebral blood flow velocity.

3. The invention of claim 2 wherein the said transcranial Doppler instrument has bilateral ultrasound probes placed on the temporal bones for manual or automatic isonation of the cerebral vessels.

4. The invention of claim 3 wherein the said device is operatively connected to a microcomputer that processes and displays the cerebral blood flow velocity signals and laterality indices.

5. The invention of claim 4 wherein the said device is operatively connected to a cellular phone circuit as means to facilitate mobility of the subject and ensure connectivity to other computers.

6. The invention of claim 5 wherein the cerebral blood flow velocity is used to determine odor match.

7. The invention of claim 6 wherein the cerebral blood flow velocity is used for odor selection based on hedonic rating.

8. The invention of claim 7 wherein the cerebral blood flow velocity is used to determine if a given odor additive evokes a desired brain response.

9. The invention of claim 8 and further including a means for administering target odors in a controlled laboratory condition.

10. The invention of claim 9 further including a means for simultaneously presenting multiple modalities comprising visual, auditory and olfactory sensing.

11. A noninvasive method to determine the cerebral blood flow velocity response to odor tasks of a canine subject, including steps of
   (a) obtaining a subject's baseline cerebral blood flow velocity in cerebral arteries on both sides of the brain using a transcranial Doppler ultrasound instrument with two probes placed on the temples and sample volumes focused on cerebral vessels on both sides;
   (b) simultaneously with (a) obtaining the mean blood flow velocity in both pairs of cerebral arteries at baseline;
   (c) testing the subject with odor tasks while simultaneously monitoring the mean blood flow velocity during each task in real-time;
   (d) determining the response of the brain using mean cerebral blood flow velocity to a target odor;
   (e) determining the response of the brain using side-to-side differences in mean cerebral blood flow velocity to a target odor;
   (f) determining the response of the brain using side-to-side differences in mean cerebral blood flow velocity to a given odor;
   (g) determining the response of the brain using side-to-side differences in mean cerebral blood flow velocity to a given odor component;
   (h) simultaneously with (g) determining if there is a match of the response of the brain using side-to-side differences in mean cerebral blood flow velocity to a given odor compared to the response evoked by target odor;
   (i) simultaneously with (h) assessing if varying the intensity of the given odor evokes a brain response similar to that during target odor;
   (j) determining the response of the brain using the laterality index calculated from mean cerebral blood flow velocity to a target odor;

(k) simultaneously with (i) determining the latency and peak variations of as laterality index during each odor task;

(l) determining the response of the brain using the latency and peak variations of laterality index calculated from mean cerebral blood flow velocity to a target odor;

(m) simultaneously with (l) determining if there is a match of the response of the brain using the latency and peak variations of laterality index calculated from mean cerebral blood flow velocity to a given odor as compared to the response evoked by target odor; and (n) simultaneously with (m) assessing if by varying the intensity of the given odor the match in response to target odor could be enhanced.

12. The invention of claim 11 wherein the said device is operatively connected to a microcomputer that processes and displays the cerebral blood flow velocity signals and laterality indices.

13. The invention of claim 12 and further including a cellular phone circuit means to connect to a forensic computer data base.

14. The invention of claim 13 and further including a means for administering target odors in a controlled forensic laboratory condition.

15. The invention of claim 14 and further including means for measuring odor working memory.

16. A noninvasive method and system to determine the cerebral blood flow velocity response to odor tasks of a subject, including steps of:

(a) obtaining a subject's baseline cerebral blood flow velocity in cerebral arteries on both sides of the brain using a transcranial Doppler ultrasound instrument with two probes placed on the temples and sample volumes focused on cerebral vessels on both sides;

(b) simultaneously with (a) obtaining the mean blood flow velocity in both pairs of cerebral arteries at baseline, (c) testing the subject with odor tasks while simultaneously monitoring the mean blood flow velocity during each task in real-time;

(d) determining the response of the brain using mean cerebral blood flow velocity to a target odor;

(e) determining the response of the brain using side-to-side differences in mean cerebral blood flow velocity to a target odor;

(f) determining the response of the brain using side-to-side differences in mean cerebral blood flow velocity to a given odor;

(g) determining the response of the brain using side-to-side differences in mean cerebral blood flow velocity to a given odor component;

(h) simultaneously with (g) determining if there is a match of the response of the brain using side-to-side differences in mean cerebral blood flow velocity to a given odor compared to the response evoked by target odor;

(i) simultaneously with (h) assessing if by varying the intensity of the given odor the match in response to target odor could be enhanced;

(j) determining the response of the brain using the laterality index calculated firm mean cerebral blood flow velocity to a target odor;

(k) simultaneously with (j) determining the latency and peak variations of laterality index during a given odor task;

(l) determining the response of the brain using the latency and peak variations of laterality index calculated from mean cerebral blood flow velocity to a target odor;

(m) determining the response of the brain using the latency and peak variations of laterality index calculated from mean cerebral blood flow velocity to a battery of odor tasks;

(n) simultaneously with (m) determining the hedonic rating for each odor;

(o) simultaneously with (n) determining if the response of the brain using the latency and blood flow velocity differentiate the odors according to hedonic ratings; and (p) simultaneously with (o) assessing the odors with high hedonic ratios.

17. The invention of claim 16 wherein the brain responses to body odor and facial makeup are used to optimize the hedonic ratings of a personality.

18. The invention of claim 17 and further including a means for administering odors in a controlled laboratory condition.

19. The invention of claim 18 and further including means for administering odors in a closed space such as a film theater.

20. The invention of claim 19 wherein the brain responses to odor and audiovisual scenes in a movie are used to optimize the real life effect of the movie.

* * * * *